(12) United States Patent
Okun et al.

(10) Patent No.: US 7,858,040 B2
(45) Date of Patent: Dec. 28, 2010

(54) DIRECT MIXING AND INJECTION FOR HIGH THROUGHPUT FLUIDIC SYSTEMS

(75) Inventors: Alex Okun, San Diego, CA (US);
Teresa A. Bennett, San Diego, CA (US);
Andrew Beernink, San Diego, CA (US);
David J. Sieg, Escondido, CA (US);
John T. Ransom, Encinitas, CA (US)

(73) Assignee: Saryna Biotechnologies LLC, San Diego, CA (US)

( * ) Notice: Subject to any disclaimer, the term of this patent is extended or adjusted under 35 U.S.C. 154(b) by 1344 days.

(21) Appl. No.: 10/841,810

(22) Filed: May 7, 2004

(65) Prior Publication Data
US 2005/0249635 A1 Nov. 10, 2005

(51) Int. Cl.
*B01L 3/02* (2006.01)
(52) U.S. Cl. .................... 422/100; 436/49; 73/864.01
(58) Field of Classification Search ............... 436/49; 422/100; 73/864.01
See application file for complete search history.

(56) References Cited

U.S. PATENT DOCUMENTS

| | | | | |
|---|---|---|---|---|
| 4,691,580 A | * | 9/1987 | Fosslien | 73/864.84 |
| 5,525,302 A | * | 6/1996 | Astle | 422/100 |
| 5,692,220 A | | 11/1997 | Diamond et al. | 395/924 |
| 5,804,436 A | | 9/1998 | Okun | 435/286.1 |
| 5,919,646 A | | 7/1999 | Okun | 435/29 |
| 6,096,509 A | | 8/2000 | Okun | 435/29 |
| 6,242,209 B1 | | 6/2001 | Ransom | 435/29 |
| 6,280,967 B1 | | 8/2001 | Ransom | 435/29 |
| 6,379,917 B1 | | 4/2002 | Okun | 435/29 |
| 6,514,722 B2 | | 2/2003 | Palsson | 435/40.5 |
| 2001/0027269 A1 | | 10/2001 | Tanaka | 600/368 |
| 2002/0170365 A1 | | 11/2002 | Sklar | 73/865.5 |
| 2003/0013201 A1 | | 1/2003 | Sklar | 436/63 |
| 2003/0040105 A1 | | 2/2003 | Sklar | 435/287.2 |
| 2004/0025575 A1 | | 2/2004 | Petro et al. | 73/61.55 |

FOREIGN PATENT DOCUMENTS

| | | |
|---|---|---|
| EP | 0 645 631 A2 | 3/1995 |
| EP | 1 229 448 | 1/2003 |
| WO | WO 01/59429 | 8/2001 |
| WO | WO 02/065121 A1 | 8/2002 |

OTHER PUBLICATIONS

Kuckuck, F. W., B. Edwards, and L. Sklar, "High throughput flow cytometry" Cytometry, 2001, 44(1): p. 83-90.

Pennings, A., P. Speth, H. Wessels and C. Haanen, "Improved flow cytometry of cellular DNA and RNA by on-line reagent addition" Cytometry, 1987, 8(3): p. 335-8.

(Continued)

*Primary Examiner*—Lyle A Alexander
(74) *Attorney, Agent, or Firm*—Knobbe Martens Olson & Bear LLP

(57) ABSTRACT

A system and method of mixing and injecting discrete sample mixtures into a flow cytometer or other sample analysis apparatus may generally comprise a sample injection guide coupling a liquid handling apparatus with a sample analysis apparatus and facilitating injection of discrete sample mixtures into a fluidic system of the apparatus.

24 Claims, 8 Drawing Sheets

OTHER PUBLICATIONS

Kelley, K.A., "Sample station modification providing on-line reagent addition and reduced sample transit time for flow cytometers" Cytometry, 1989, 10(6) 796-800, abstract only.

Kelley, K.A., "Very early detection of changes associated with cellular activation using a modified flow cytometer" Cytometry, 1991, 12(5): p. 464-8.

Lindberg, W., J. Ruzicka, and G. Christian, "Flow injection cytometry: a new approach for sample and solution handling in flow cytometry" Cytomertry, 1993, 14(2): p. 230-6.

Lindberg, W., L. Scampavia, J. Ruzicka and G. Christian, "Fast kinetic measurements and on-line dilution by flow injection cytometry" Cytometry, 1994, 16(4): p. 324-30.

Scampavia, L. D., G. Blankenstein, J. Ruzicka and G. Christian, "A coaxial jet mixer for rapid kinetic analysis in flow injection and flow injection cytometry" Anal. Chem., 1995, 67(17): p. 2743-9.

Blankenstein, G., L. Scampavia, J. Ruzicka and G. Christian, "Coaxial flow mixer for real-time monitoring of cellular responses in flow injection cytometry" Cytometry, 1996, 25(2): p. 200-4.

Dunne, J. F., "Time window analysis and sorting" Cytometry, 1991, 12(7): p. 597-601.

Steen, H. B., "A sample injection device for flow cytometers" Cytometry, 2002, 49(2): p. 70-2.

Abu-Absi, N. R., A. Zamamiri, J. Kacmar, S. Balogh and F. Sriene, "Automated flow cytometry for acquisition of time-dependent population data" Cytometry, 2003, 51A(2): 87-96.

Ramirez, S., C. Aiken, B. Andrzejewski, L. Sklar, and B. Edwards, "High-throughput flow cytometry: Validation in microvolume bioassays" Cytometry, 2003, 53A: p. 55-65.

JCSMR Flow Cytometry "An Introduction" http://jcsmr.anu.edu.au/facslab/intro.html.

Edwards, B. S., F. Kuckuck and L. A. Sklar, "Plug flow cytometry: An automated coupling device for rapid sequential flow cytometric sample analysis" Cytometry, 1999, 37 (2); p. 156-9.

Edwards, B., F. Kuckuck, E. Prossnitz, A. Okun, J. Ransom and L. Sklar, "Plug flow cytometry extends analytical capabilities in cell adhesion and receptor pharmacology" Cytometry, 2001 43(3), p. 211-6.

Edwards, B., F. Kuckuck, E. Prossnitz, J. Ransom and L. Sklar, "HTPS flow cytometry; a novel platform for automated high throughput drug discovery and characterization" J. Biomol. Screen., 2001, 6(2), p. 83-90.

Ransom, J.T., B. Edwards, F. Kuckuck, A. Okun, D. Mattox, E. Prossnitz and L. Sklar, "Flow cytometry systems for drug discovery and development" Optical Diagnostics for Living Cells, III Daniel L. Farkas, Robert C. Leif, editors, Proceedings of SPIE vol. 3921, 2000, p. 90-100.

Jackson, W. C., F. Kuckuck, B. Edwards, A. Mammoli, C. Gallegos, G. Lopez, T. Buranda and L. Sklar, "Mixing small volumes for continuous high-throughput flow cytometry: Performance of a mixing Y and peristaltic sample delivery" Cytomerty, 2002, 47(3): p. 183-91.

* cited by examiner

US 7,858,040 B2

DIRECT MIXING AND INJECTION FOR HIGH THROUGHPUT FLUIDIC SYSTEMS

STATEMENT REGARDING FEDERALLY SPONSORED RESEARCH AND DEVELOPMENT

This application was funded by the following grants: 2R44DK057966-02 from the National Institute of Diabetes & Digestive & Kidney Diseases ("NIDDK"), 5R44DK057966-03 also from the NIDDK and 5R01AI048517-03 from the National Institute of Allergy and Infectious Diseases ("NIAID").

FIELD OF THE INVENTION

Aspects of the present invention relate generally to the fields of flow cytometry and fluorescence activated cell sorting (FACS), and more particularly to a system and method of mixing and injecting discrete sample mixtures into a flow cytometer or other sample analysis apparatus.

BACKGROUND

One frequently used technique in modern drug discovery involves exposing cells bearing a specific drug discovery target to collections of test compounds so that the effect of the various compounds on the cells, through interaction with the expressed specific target, may be evaluated. In typical techniques, the cells are labeled with an indicator material, such as a fluorescent substrate that signals a signal transduction event, allowing the qualitative and/or quantitative nature of the compound and target interaction to be assessed by an instrument which indicates that the target has been contacted by the compound and, more particularly, measures specific properties of the substrate. Information derived from such assays may generally be used to assign relative activity levels to the various compounds being tested. To expand the breadth of information regarding the most active chemical structures, such assays are often performed with large chemical libraries, or with focused but diverse libraries, and employing medium to high throughput methodologies using automated or robotic systems such as liquid handlers and multi-well plate readers.

Flow cytometers, often referred to as fluorescence activated cell sorting (FACS) apparatus, are unique instruments that utilize fluidic systems to align cells in single file; in accordance with conventional flow cytometry technology, the cells are passed at relatively high speeds across intersecting beams of light having specific spectral properties. For example, flow cytometers commonly use coherent laser beams from one or more sources (each having distinct spectral laser lines) to excite specific fluorochromes, such as a signal transduction indicator material, with unique spectral properties on or in the cells. In some circumstances, flow cytometers may offer significant advantages over other analytical instruments such as may be implemented in single cell analyses and spectrally multiplexed measurement applications. On the other hand, flow cytometers have not typically been successfully combined with automated sample mixing and injection mechanisms, particularly systems that allow target-bearing cells to be mixed with test compounds and subsequently injected into the fluidic system of the flow cytometer. In that regard, conventional flow cytometer and other sample analysis techniques are deficient at least to the extent that they are inherently associated with substantial carryover of compound or sample material from one sample to the next, they are generally characterized by relatively low throughput rates, or both.

SUMMARY

Embodiments of the present invention overcome the foregoing and various other shortcomings of conventional fluidic sample analysis technologies, providing a system and method of mixing and injecting discrete sample mixtures into a flow cytometer or other sample analysis apparatus. In accordance with some exemplary embodiments, for example, a sample injection guide may couple a liquid handling apparatus with a sample analysis apparatus, facilitating injection of discrete sample mixtures into a fluidic system of the apparatus.

As set forth in more detail below, a sample analysis system may generally comprise: a liquid handling apparatus operative to prepare a discrete sample mixture; a sample analysis apparatus; and an injection guide coupled to the analysis apparatus; the injection guide operative to receive the discrete sample mixture from the liquid handling apparatus and to provide the discrete sample mixture to a fluidic system of the analysis apparatus. In accordance with some embodiments, the injection guide may comprise: a guide well operative to engage a pipette tip manipulated by the liquid handling apparatus; and a port in fluid communication with the guide well and operative to receive the discrete sample mixture from the pipette tip and to communicate the discrete sample mixture to the fluidic system. The guide well and the port may be in continuous fluid communication with the fluidic system.

Embodiments are disclosed wherein the liquid handling apparatus comprises a single arm liquid handler; additional embodiments are disclosed wherein the liquid handling apparatus comprises a multiple arm liquid handler, such as an apparatus that employs two pipetting arms.

A sample analysis system may further comprise a cell suspension system operative to maintain sample cell material at a substantially constant density throughout a volume of suspension medium. In accordance with one exemplary embodiment, the cell suspension system comprises: a suspension vessel containing the sample cell material and the suspension medium; and a rocking apparatus operative to agitate the sample cell material and the suspension volume in the suspension vessel. The suspension vessel may be embodied in or comprise a sealed tube having an aperture; the aperture allowing a component of the liquid handling apparatus, such as a pipette tip, for example, to withdraw a volume of the sample cell material and the suspension volume from the tube.

Systems are disclosed wherein the sample analysis apparatus comprises a flow cytometer, though other analysis apparatus are contemplated and readily substituted in place of the flow cytometer.

In accordance with another aspect of the present disclosure, embodiments of a sample injection guide may generally comprise: a guide well operative to engage a pipette tip; and a port operative to receive contents of the pipette tip engaged with the guide well and to communicate the contents to an independent fluidic system.

As set forth in detail below, the guide well and the port may be in continuous fluid communication with the independent fluidic system. In one exemplary embodiment having utility in this implementation, the sample injection guide further comprises: an overflow well in fluid communication with the guide well and operative to receive excess liquid back flushed into the guide well through the port from the independent fluidic system when the pipette tip is disengaged from the guide well. Additionally, the sample injection guide may further comprise a siphon port in fluid communication with the overflow well and operative to communicate the excess liquid to a waste container; moreover, the sample injection guide may further comprise a pump coupled to the siphon port and facilitating communication of the excess liquid to the waste container.

In accordance with one exemplary embodiment, a method of providing discrete sample mixtures to a sample analysis apparatus may generally comprise: coupling an injection guide to the sample analysis apparatus; the injection guide in fluid communication with a fluidic system of the sample analysis apparatus; preparing a discrete sample mixture; and utilizing the injection guide to provide the discrete sample mixture to the fluidic system. As set forth in detail below, the preparing may comprise employing an automated liquid handling apparatus; the employing, in turn, may comprise utilizing a single arm or a multiple arm pipetting apparatus.

The coupling in some embodiments comprises allowing a guide well and a port associated with the injection guide to be in continuous fluid communication with the fluidic system; in that regard, the method may further comprise allowing excess liquid to back flush into the guide well through the port from the fluidic system. Some methods of providing discrete sample mixtures to a sample analysis apparatus may further comprise communicating the excess liquid to a waste container; in the illustrated embodiments, the communicating comprises utilizing a siphon port integrated into the injection guide, though other communicating methodologies may be readily implemented. The communicating may additionally comprise utilizing a pump coupled to the siphon port.

In accordance with some embodiments, a computer readable medium may be encoded with data and instructions for providing a discrete sample mixture to a sample analysis apparatus; the data and the instructions causing an apparatus executing the instructions to: prepare a discrete sample mixture; and provide the discrete sample mixture to a fluidic system of the sample analysis apparatus through an injection guide coupled to the sample analysis apparatus. The preparation of the sample mixture and general constitution of the injection guide may be implemented as in the foregoing embodiments.

The computer readable medium may further cause an apparatus to employ an automated liquid handling apparatus in preparing the discrete sample mixture; as in the foregoing embodiments, the computer readable medium may cause an apparatus to utilize a single arm pipetting apparatus or a multiple arm pipetting apparatus in this context. Additionally, the computer readable medium may further cause an apparatus executing the instructions to record data associated with the discrete sample mixture.

In accordance with other embodiments, a computer readable medium may be encoded with data and instructions for performing an analysis of a discrete sample mixture; the data and the instructions causing an apparatus executing the instructions to: acquire a first data set associated with a discrete sample mixture from an injection system; acquire a second data set from an analysis apparatus; compare the first data set with the second data set to correlate data records with the discrete sample mixture; perform an analysis on the data records associated with the discrete sample mixture; and record results of the analysis. The computer readable medium may further cause an apparatus executing the instructions to transmit the results. Additionally or alternatively, the computer readable medium may further cause an apparatus executing the instructions to perform the analysis using a statistical analytical method.

The foregoing and other aspects of the disclosed embodiments will be more fully understood through examination of the following detailed description thereof in conjunction with the drawing figures.

DETAILED DESCRIPTION

Figure 1:
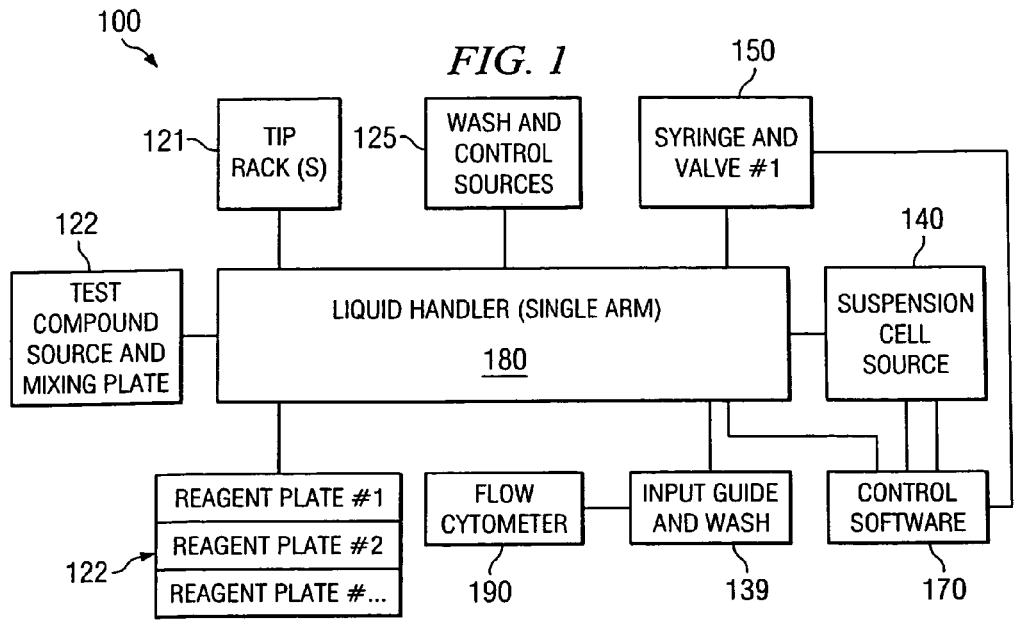
FIG. 1 is a simplified block diagram illustrating functional components of one embodiment of a sample analysis system incorporating elements of a direct sample injection system.
Figure 2:
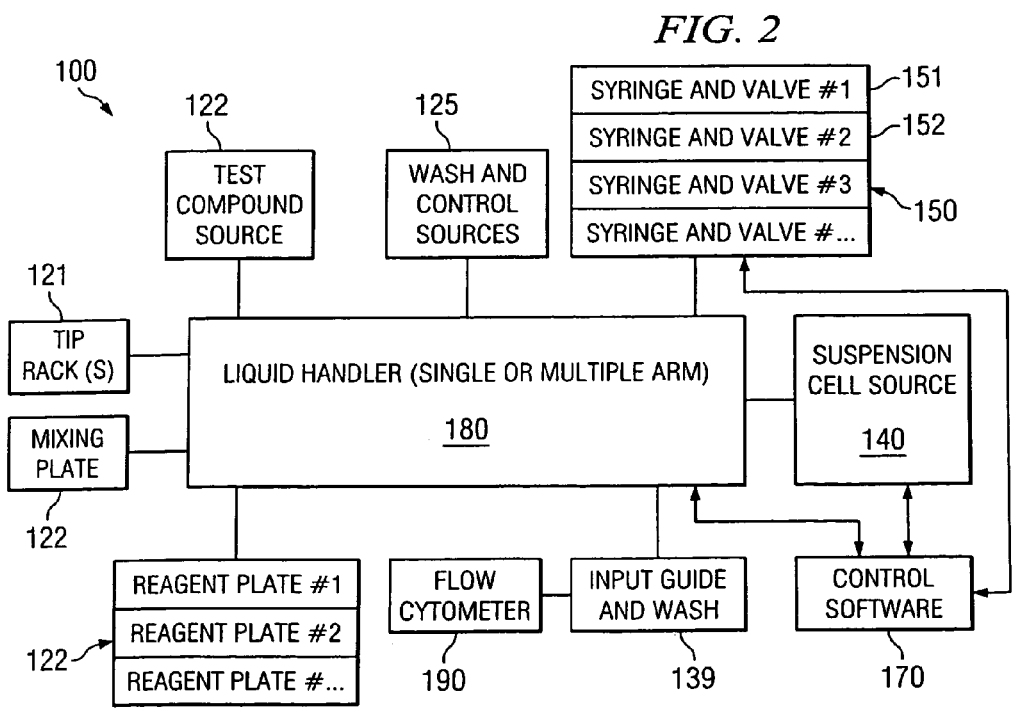
FIG. 2 is a simplified block diagram illustrating functional components of another embodiment of a sample analysis system incorporating elements of a direct sample injection system.

Turning now to the drawing figures, FIG. 1 is a simplified block diagram illustrating functional components of one embodiment of a sample analysis system incorporating elements of a direct sample injection system, and FIG. 2 is a simplified block diagram illustrating functional components of another embodiment of a sample analysis system incorporating elements of a direct sample injection system.

The functional description set forth below is primarily directed to operational characteristics of the FIG. 2 embodiment which may employ a dual pipetting arm liquid handler arrangement, though a single pipetting arm arrangement, such as illustrated in FIG. 1, may also have utility in various applications. Those of skill in the art will appreciate that a sample analysis system as contemplated herein may be susceptible of numerous alterations and modifications, and that the particular configuration of structural components may be selectively adjusted in accordance with myriad considerations including, but not limited to: overall system requirements; size or scale limitations of one or more structural elements; implementation, programming instructions, and computational bandwidth of various processing components; desired sample throughput rates; and other factors. In particular, the present disclosure is not intended to be limited by the number of articulated arms employed by any particular liquid handler apparatus.

As illustrated in FIGS. 1 and 2, an exemplary sample analysis system 100 generally comprises an analysis apparatus such as a flow cytometer 190, for example, and a liquid or sample handling and injection system, such as liquid handler 180. As contemplated herein, references to "direct sample injection" and similar terms are generally related to a process of delivering discrete sample mixtures from liquid handler 180 to an independent fluidic system such as may be incorporated or integrated in a sample analysis apparatus (e.g., flow cytometer 190); it will be appreciated that, in this context, the term "independent" generally refers to a fluidic system of a sample analysis apparatus that is distinct from, or not necessarily integrated with, the structure (in general) and the fluidic system (in particular) associated with liquid handler 180, though used in conjunction therewith in system 100.

In some embodiments, flow cytometer 190 may be implemented in fluorescence activated cell sorting (FACS) applications; additionally or alternatively, flow cytometer 190 may be employed in any of various sample analysis applications generally known in the art or developed and operative in accordance with known principles. In alternative implementations of system 100, flow cytometer 190 may be supplemented or replaced by any of various different types of sample analysis apparatus benefiting from direct sample injection functionality as set forth in more detail below. For example, one such alternative apparatus may include suitable structural elements allowing or enabling various microfluidic applications; those of skill in the art will appreciate that a direct sample injection system may have utility in numerous environments with minimal or no modification.

During use, liquid handler 180 may be operative (under microprocessor or computer control, for example) to prepare samples to be analyzed and to deliver sample material or other liquid mixtures to a flow cytometer 190 or another sample analysis apparatus through a sample injection guide component 139. In that regard, liquid handler 180 in the FIG. 2 arrangement may be embodied in or incorporate any of various commercially available, computer or microprocessor controlled, dual arm liquid handling stations such as, for example, a Cavro RSP 9000 unit; similarly, the FIG. 1 liquid handler 180 may be embodied in or comprise any single arm liquid handling station such as may be generally available or as may be developed and operative in accordance with the functional characteristics set forth herein.

Figure 13:
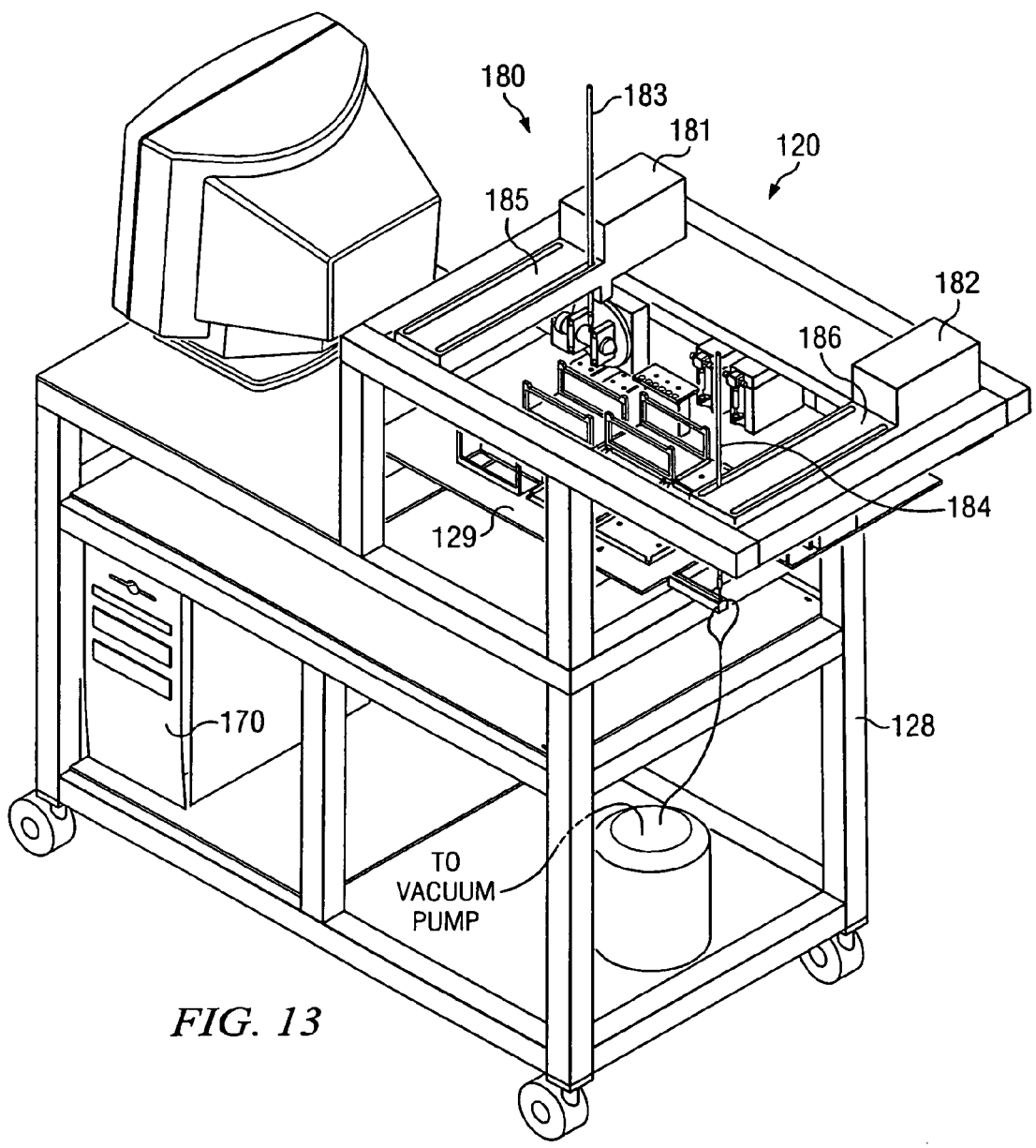
FIG. 13 is a simplified perspective diagram illustrating components of one embodiment of a sample analysis system incorporating a direct sample injection system.
Figure 14:
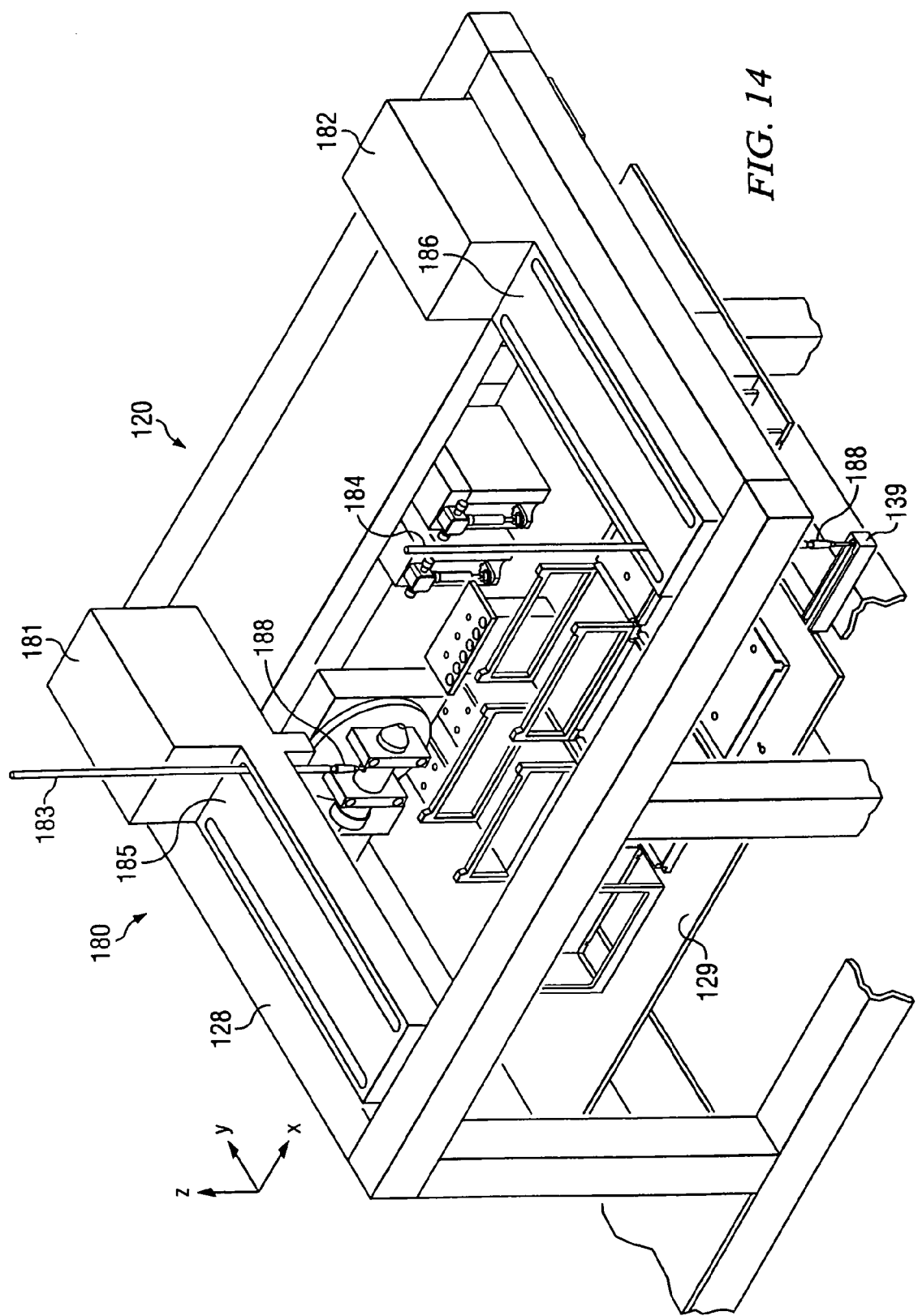
FIG. 14 is a simplified perspective diagram illustrating components of one embodiment of a direct sample injection system.
Figure 15:
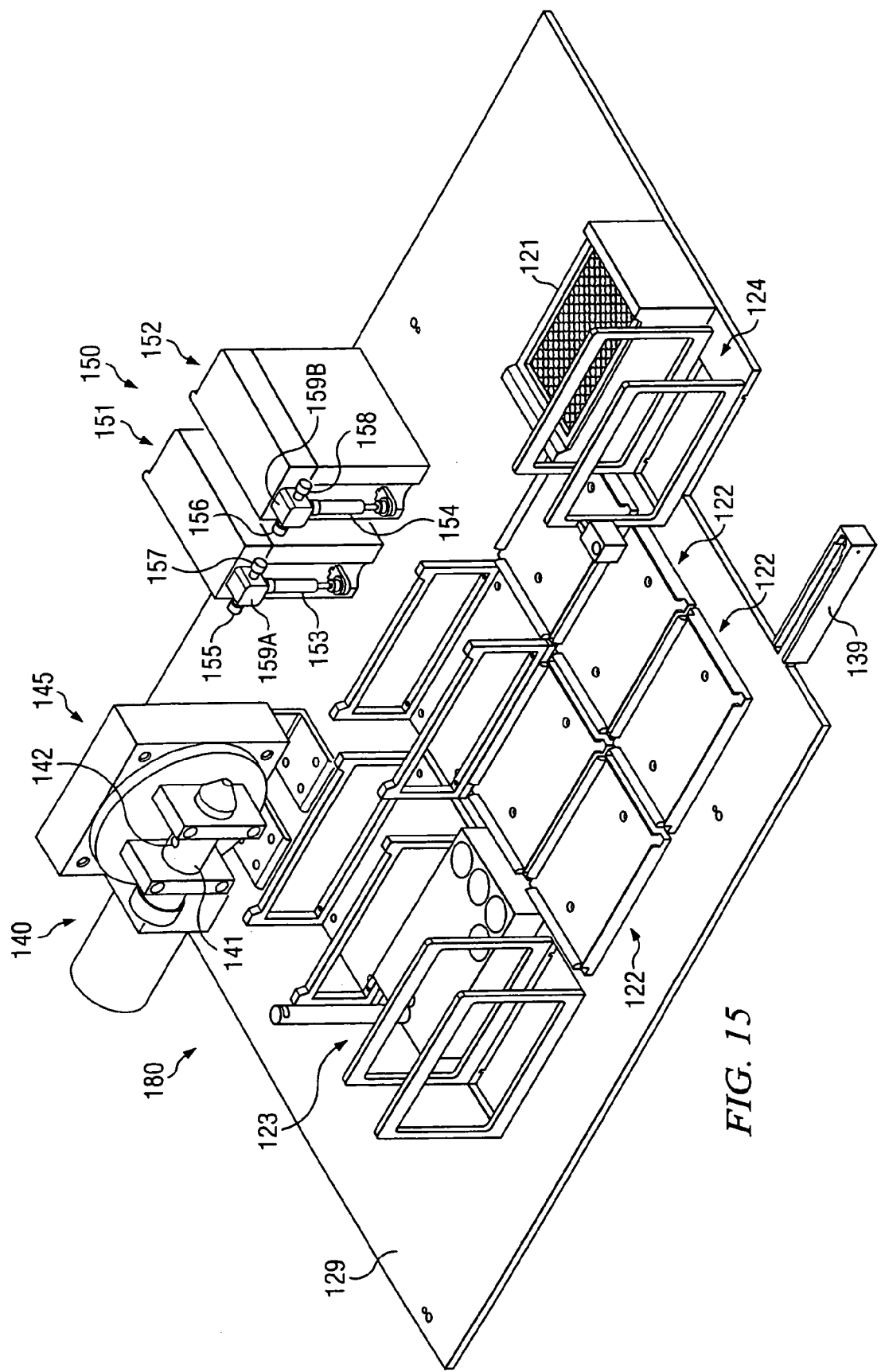
FIG. 15 is a simplified perspective diagram illustrating additional components of the direct sample injection system of FIG. 14.

With reference now to FIGS. 13-15 in addition to FIGS. 1 and 2, it is noted that FIG. 13 is a simplified perspective diagram illustrating components of one embodiment of a sample analysis system incorporating a direct sample injection system, FIG. 14 is a simplified perspective diagram illustrating components of one embodiment of a direct sample injection system, and FIG. 15 is a simplified perspective diagram illustrating additional components of the direct sample injection system of FIG. 14.

Liquid handler 180 may generally be configured and operative to implement disposable pipette tips on any number of pipetting arms; as set forth above, while the exemplary embodiment of FIGS. 2, 13, and 14 employs two pipetting arms (reference numerals 181 and 182), systems incorporating one arm (FIG. 1), as well as systems incorporating more than two arms, are also contemplated. Such systems employing an arbitrary number of pipetting arms may be implemented in accordance with the principles and functional attributes described herein. In the exemplary system 100, a respective pipetting probe 183,184 may be suspended from a respective translational support structure 185,186 associated with each respective arm 181,182. Such pipetting arm assemblies accommodate rapid, precise movement of probes 183, 184 in x, y, and z (i.e., Cartesian) coordinate directions. For many applications, translation in approximately 0.003 inch (0.076 mm) increments in a particular coordinate direction may readily be achieved using conventional automated or microprocessor controlled liquid handlers; such precision may be sufficient, but may not be necessary, for typical uses. It will be appreciated that the degree of precision with which a pipetting arm (181,182) and its associated support structure (185,186) and probe (183, 184) are moved may be a function of various factors; the present disclosure is not intended to be limited by parameters affecting accurate and precise placement of structural elements in traditional liquid handling systems.

Pipetting arm 181,182, structure 185,186, and probe 183, 184 combinations are generally operative to manipulate probes 183,184 in three-dimensional space, enabling probes 183,184 selectively to engage a pipette tip (reference numeral 188 in FIG. 14) which may be fabricated of plastic, acrylic, latex, or other suitable materials as generally known in the art. In that regard, probe 183,184 may be lowered into a rack of pipette tips (reference numeral 121) for coupling of probe 183,184 with a cooperating pipette tip 188. Some such pipette tips 188 currently available may have, for example, a fluid volume capacity of about 20-1000 µl (e.g., Tecan Genesis tips, from VWR/Quality Scientific Products, are available in the foregoing capacity range, and may be suitable for various applications involving automated or semi-automated pipetting procedures).

Figure 6:
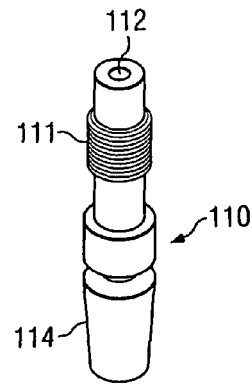
FIG. 6 is a simplified diagram illustrating a perspective view of one embodiment of a coupling component allowing a pipette probe to engage a pipette tip.
Figure 7:
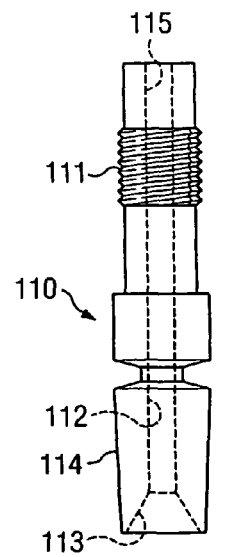
FIG. 7 is a simplified diagram illustrating a side elevation view of the coupling component embodiment of FIG. 6.
Figure 9:
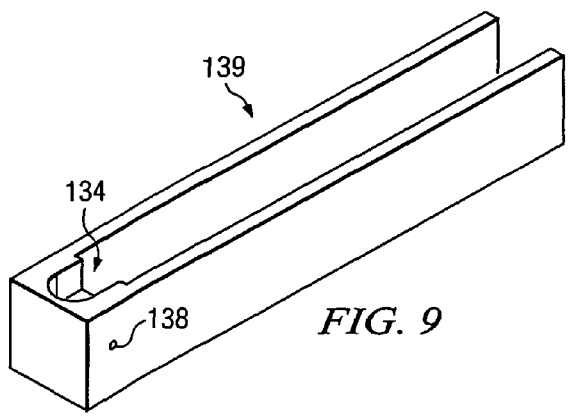
FIG. 9 is a simplified diagram illustrating a perspective view of one embodiment of a sample injection guide.
Figure 8:
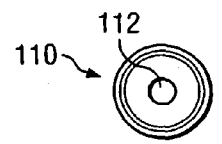
FIG. 8 is a simplified diagram illustrating an axial view of the coupling component embodiment of FIG. 6.
Figure 10:
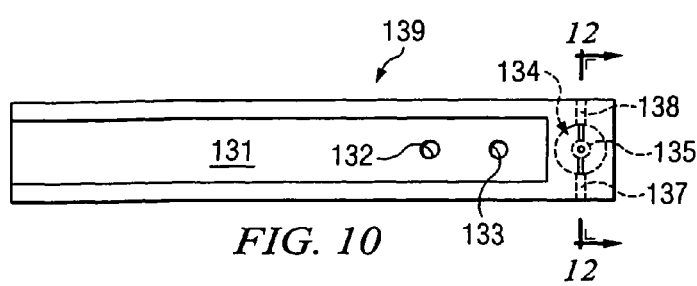
FIG. 10 is a simplified diagram illustrating a plan view of the sample injection guide embodiment of FIG. 9.
Figure 11:
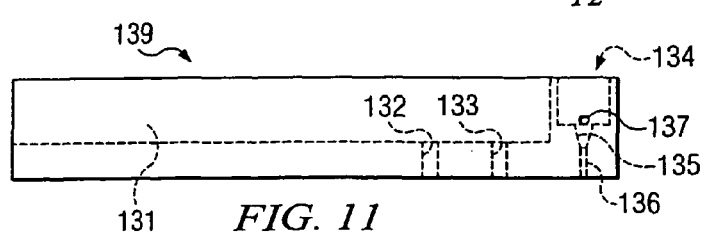
FIG. 11 is a simplified diagram illustrating a side elevation view of the sample injection guide embodiment of FIG. 9.
Figure 12:
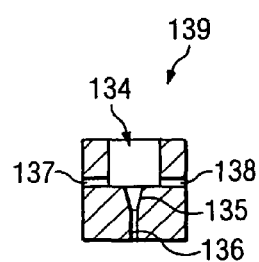
FIG. 12 is a simplified diagram illustrating an axial cross-section view of the sample injection guide embodiment of FIG. 9 taken on the line 12-12 in FIG. 10.

In some embodiments, a coupling structure or component may facilitate coupling of probe 183,184 with a particular type of pipette tip 188 having known structural dimensions. Specifically, FIGS. 6, 7, and 8 are simplified diagrams illustrating perspective, side elevation, and axial views, respectively, of one embodiment of a coupling component allowing a pipette probe to engage a pipette tip. As illustrated in FIGS. 6-8, a coupling component 110 may generally comprise a conduit 112 through which fluid may be communicated. Coupling component 110 may be fabricated of plastic (such as DELRIN™, for example), acrylic, metal, or other material having suitable strength, rigidity, and corrosion resistance characteristics, for example, which may be application-specific.

Coupling component 110 may comprise an appropriate structural element configured and operative to secure coupling component 110 to probe 183,184; specifically, probe 183,184 and coupling component 110 may be sealingly engaged, preventing leakage or other liquid loss at the juncture therebetween. In the exemplary embodiment, structural coupling or interconnection between probe 183,184 and coupling component 110 is represented as effectuated at a threaded portion 111. It will be appreciated, however, that coupling of probe 183,184 and coupling component 110 may be achieved using other structural elements such as, for example, a quick-disconnect mechanism, a hose barb, or other coupling device having utility in fluidic systems.

Similarly, coupling component 110 may additionally comprise an appropriate structural element configured and operative to secure pipette tip 188 to coupling component 110; as with the connection set forth above, coupling component 110 and pipette tip 188 may be sealingly engaged, preventing leakage or other liquid loss at the juncture therebetween. In the exemplary embodiment, structural coupling or interconnection between coupling component 110 and pipette tip 188 is represented as effectuated at an angled portion 114 operative (e.g., like a hose barb) to engage, under pressure, a cooperating open end of pipette tip 188 having a correspondingly angled inside diameter dimension as generally known in the art. It will be appreciated that coupling of pipette tip 188 and coupling component 110 may be achieved using other structural elements having utility in fluidic systems. In some embodiments implementing automated liquid handling apparatus and techniques, coupling component 110 may additionally allow or enable automated ejection (i.e., disengagement or decoupling) of pipette tip 188 from angled portion 114.

During pipetting operations when coupling component 110 is interposed between probe 183,184 and pipette tip 188, liquid may be communicated from probe 183,184 into conduit 112, and vice-versa, at end 115; similarly, liquid may be communicated from conduit 112 to pipette tip 188, and vice-versa, at end 113. It will be appreciated that the various elements, in general, and the specific structural arrangement, in particular, of coupling component 110 may be susceptible of various modifications, and that aspects of the exemplary structure depicted in FIGS. 6-8 may be selectively dimensioned, altered, omitted, or rearranged in accordance with numerous considerations including, but not limited to, the dimensions and other structural characteristics of probes 183, 184, pipette tip 188, or both. For example, where probes 183,184 and pipette tip 188 are suitably constructed for direct coupling or other unassisted engagement, it may be possible to omit coupling component 110 from the fluidic path (i.e., coupling component 110 may not be required for proper operation of some embodiments of liquid handler 180).

As illustrated in FIGS. 1 and 2, a sample analysis system 100 may generally comprise a pump system 150 configured and operative to control fluid flow and liquid handling procedures. As indicated in FIGS. 2 and 15, the pipetting function for each respective pipetting arm 181,182 and probe 183,184 assembly may be driven or otherwise influenced by a respective pump system 151,152. In the exemplary implementation, pump systems 151,152 may be embodied in or comprise computer or microprocessor controlled, servo motor driven syringe and diverter valve systems in fluid communication with the interior of probes 183,184 through flexible tubing, for example, or through some other suitable fluidic path or conduit. One exemplary apparatus, the Hamilton PSD3 Servo syringe pump, is commercially available and may be suitable for use in accordance with the present disclosure.

In operation, a syringe motor (not shown in FIG. 15) may receive commands from control software, firmware, or other programming instruction sets; in FIGS. 1, 2, and 13, such control functionality is represented generally by the reference numeral 170. Accordingly, the syringe motor may be instructed selectively to withdraw a syringe plunger (e.g., to load a syringe 153,154) or to advance the syringe plunger (e.g., to expel contents of syringe 153,154). In some systems, a diverter valve 159A,159B may also receive commands from control software or some other processing and control component 170 (i.e., hardware, firmware, or software). In that regard, diverter valve 159A,159B may be instructed selectively to allow communication of liquids between syringe 153,154 and a buffer supply source (reference numeral 125 in FIGS. 1 and 2), for example, through a port 155,156, or between syringe 153,154 and probes 183,184 through an alternative port 157,158.

The foregoing arrangement allows syringes 153,154 to fill with an appropriate buffer material (such as PBS or HBSS, for instance) or with other chemical or biological reagents, and selectively to drive the fluid contents of syringes 153,154 through the interior (conduit 112) of coupling component 110 and into or through pipette tip 188 as set forth in more detail below. In particular, the volume of material drawn into or dispensed from pipette tip 188 coupled to a respective probe 183,184 may be controlled (e.g., under hydraulic control) by selective operation of respective pump systems 151,152.

The foregoing operation and various other functional characteristics of system 100 may be controlled by processing component 170. In that regard, processing component 170 may be embodied in or comprise one or more computers, microprocessors or microcomputers, microcontrollers, programmable logic controllers, field programmable gate arrays, or other suitably configurable or programmable hardware components. In particular, processing component 170 may comprise hardware, firmware, software, or some combination thereof, configured, appropriately programmed, and operative selectively to control operational parameters or otherwise to influence functionality of components of system 100. It will be appreciated that processing component generally comprises a computer readable medium encoded with data and instructions, these data and instructions causing an apparatus (such as any of the various components of system 100, in general, and liquid handler 180, in particular) executing the instructions to perform some or all of the functionality set forth herein.

Parameters which may be affected or controlled by processing component 170 may include, but are not limited to, the following: timing of movement and precise three-dimensional positioning of arms 181,182, support structures 185, 186, probes 183,184, and more particularly, some combination thereof; timing and precise control of pump systems 151,152 including syringes 153, 154 and valve assemblies 159A,159B, influencing the volume of fluid in pipette tips 188 and the destination thereof; timing and characteristics of mixing operations (as set forth below); sample injection rates through guide 139 and to an independent fluidic system; and other factors.

Accordingly, processing component 170 may be capable of transmitting control signals or other instructions to various other electrical or electromechanical system elements; it will be appreciated that cooperating electrical and mechanical elements (such as motors, servos, actuators, racks and pinions, gearing mechanisms, and other interconnected or engaging dynamic parts, for example) have been generally omitted from the drawing figures for clarity, as have the various electrical connections and wiring therebetween. In that regard, those of skill in the art will appreciate that control signals may be transmitted from, and feedback from various electromechanical components may be received by, processing component 170 in accordance with any of various communication technologies and protocols having utility in interconnecting or otherwise coupling computer peripheral devices and other electronic components. Specifically, devices implemented in system 100 may be coupled to enable uni- or bi-directional data communication using serial or Ethernet connections, for example, or other standards such as Universal Serial Bus (USB) or Institute of Electrical and Electronics Engineers (IEEE) Standard 1394 (i.e., "FireWire") connections, and the like. In some embodiments, such coupled components may employ wireless data communications techniques such as BLUETOOTH™, for example, or other forms of wireless communication technologies based upon infrared (IR) or radio frequency (RF) signals.

As indicated in FIGS. 13 and 14, an automated pipetting arm assembly 120 including liquid handler 180 may be mounted on a frame 128, allowing pipetting arm 181,182 and probe 183,184 assemblies to address several different stations (e.g., pipette tip rack station 121, a microwell plate station 122, a tube station 123, and a waste bag station 124) selectively positioned or disposed on a deck or platform 129 generally positioned below arms 181,182. Frame 128 and platform 129 may be constructed of metal (such as aluminum or steel, for example), plastic, acrylic, fiberglass, or other suitably rigid material capable of bearing weight of arms 181,182 and other components of liquid handler 180, pump systems 151,152, stations 121-124, and attendant hardware or consumables disposed thereon.

In particular, as noted above, platform 129 may support several selectable stations 121-124. Examples of the stations include, but are not limited to the following: a microwell plate station (such as indicated at 122) for test compounds; a microwell plate station (such as indicated at 122) for mixing the cells and compounds where wells may or may not contain dilution buffer or test compounds at the outset; a rack containing tubes (such as indicated at 123) for holding buffers, probes, or compound standards; waste bag stations (such as indicated at 124) for discarding tips and for expelling priming buffer from probes 183,184; and racks (such as indicated at 121) for holding predispensed trays of pipette tips. It will be appreciated that various other types of stations accommodating different consumables or other items having utility in experimentation may also be included; further, the specific number and orientation of the various stations 121-124 may be altered in accordance with desired system capabilities or application requirements.

As indicated in FIG. 15, platform 129 may additionally support a sample injection guide 139. In that regard, FIGS. 9, 10, 11, and 12 are simplified diagrams illustrating perspective, plan, side elevation, and axial cross-section views, respectively, of one embodiment of a sample injection guide. In some embodiments, guide 139 may be rigidly or fixedly attached to platform 129 or to some other structural element of frame 128. The attachment may be substantially permanent, for example, such as may be achieved by welds, rivets, pressure or heat sensitive adhesives, or other substantially permanent attachment mechanism; alternatively, guide 139 may be removably attached to platform 129 or frame 128 such as by screws, bolts, tabs and slots, or other cooperating structural arrangements, for example. It will be appreciated that a removable or adjustable attachment mechanism may provide flexibility for various applications. In some alternative embodiments, guide 139 may be attached, coupled, incorporated, or otherwise integrated into the structure of flow cytometer 190 or other sample analysis apparatus. In such embodiments, it may be desirable to modify or otherwise to adjust the dimensions or relative positioning of platform 129, other components of frame 128, or some combination thereof, to allow engagement of pipette tip 188 with guide 139 as set forth in detail below.

Figure 5:
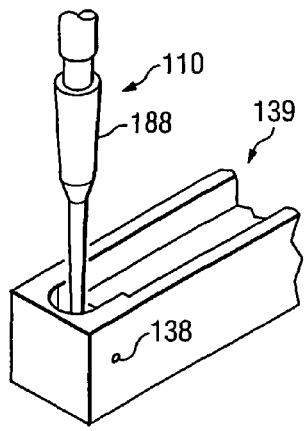
FIG. 5 is a simplified diagram illustrating a perspective view of one embodiment of a sample injection guide engaged with a pipette tip during use.

FIG. 5 is a simplified diagram illustrating a perspective view of one embodiment of a sample injection guide engaged with a pipette tip during use. Specifically, guide 139 may be constructed and operative to engage an end of pipette tip 188 and to communicate fluid from pipette tip 188 to the fluidic system of flow cytometer 190 or another sample analysis apparatus. A detailed description of one embodiment of guide 139, as well as some functional characteristics thereof, is provided below.

General Functionality

As set forth in detail above with specific reference to FIGS. 2 and 13-15, functional and mechanical drawings illustrate various components of one embodiment of a sample analysis system 100 employing a dual arm direct sample injection system; the functional attributes of a simpler, single arm embodiment (FIG. 1), as well as those of more complicated embodiments employing more than two pipetting arms, will be readily inferred from the following detailed description of operational characteristics.

Each respective arm 181,182, support structure 185,186, and probe 183,184 assembly may selectively visit tip rack 121 (or a selected, designated, or predetermined one of a plurality of tip racks 121, for example), seal a pipette tip 188 onto the end of each respective probe 183,184, and withdraw the sealed pipette tip 188 in preparation for movement to another station 122-124 on platform 129. As set forth above, probe 183,184 (either in conjunction with coupling component 110 or independently, for example) may form a sufficiently complete seal with pipette tip 188 to allow pipette tip 188 to be withdrawn from tip rack 121 without falling off when probe 183,184 is withdrawn. In particular, such a seal may also be sufficiently complete to prevent air or fluid leakage when fluids are moved into pipette tip 188 from either a reservoir or from a respective pump system 151,152—as described above with particular reference to FIG. 15, pump systems 151,152 may provide fluid (through probes 183,184) and drive volume aspiration and displacement for pipette tip 188.

Coupling component 110 may provide improved sealing between pipette tip 188 and probes 183,184. In one embodiment, for example, coupling component 110 may be fabricated of DELRIN™ plastic, though other plastics, acrylics, fiberglass, and other materials may also be suitable. Coupling component 110 may be constructed to precise dimensional specifications, and may generally be designed and operative to accommodate disposable pipette tips 188 from approximately 20 μl to approximately 1000 μl volume capacity. As set forth above with specific reference to FIGS. 6-8, different disposable pipette tip 188 products may require or substantially benefit from different specifications and structural composition of coupling component 110.

In operation, pipetting arm 182 may be used to inject successive discrete sample mixtures into flow cytometer 190 through guide 139. Initially, arm 182 may position probe 184 at a waste bag station 124, or at some other designated or selected waste vessel location; the attached pipette tip 188 may then be filled entirely (i.e., until a small excess amount is expelled as waste) with working liquid (e.g., buffer). In some embodiments, a desired buffer solution may be drawn through port 156 from a buffer reservoir (reference numeral 125 in FIGS. 1 and 2) into syringe 154. As set forth above, the selective connectivity of syringe 154 with buffer reservoir 125 or the pipette fluid path (via ports 156,158, respectively) may generally be controlled by valve 159B in line with syringe 154; accordingly, the contents of syringe 154 may then be provided to probe 184 and pipette tip 188 through port 158. Filling pipette tip 188 entirely with buffer may remove compressible air bubbles from pipette tip 188 and prevent a discrete sample mixture from being displaced back up into pipette tip 188 during later operations, for example, upon engagement of tip 188 with guide 139 when positive pressure from the fluidic system of flow cytometer 190 communicates with the contents of pipette tip 188. In some simplified dual arm liquid handling embodiments, arm 182 may be used strictly for retrieving discrete sample mixtures from selected locations on platform 129 and successively injecting these discrete sample mixtures into flow cytometer 190 or another analysis apparatus.

In coordinated or substantially simultaneous operations, pipetting arm 181 may also have buffer fluid within the tubing path (i.e., through probe 183 and to pipette tip 188). As described above with specific reference to arm 182, this fluid flow may be regulated through selective operation of syringe 153 and valve 159A of pump system 151. Such buffer fluid may facilitate reduction of compressible air in the tubing path of arm 181. In embodiments where probe 183 of arm 181 does not communicate with the high pressure fluidic system of a sample analysis apparatus (i.e., does not couple or engage pipette tip 188 with guide 139), the buffer solution may not be required to fill pipette tip 188. In the exemplary dual arm liquid handling embodiments, arm 181 may be employed to retrieve cell samples from a cell suspension system (described below) and to dispense these samples into an assay or microwell plate at a selected station 122 on platform 129, to retrieve compounds or buffer solution from one or more additional stations 122 at predetermined locations on platform 129 and to dispense same into an assay or microwell plate at a specific station 122 on platform 129, and to perform mixing functions (e.g., mixing the cell samples with compounds, mixing compounds with diluting reagents, or both).

Timing of movements for arm 181 may be keyed off the priorities and movements of arm 182. Specifically, to prevent collisions between arms 181,182, movement conflicts may be resolved, for example, by providing priority to arm 182; in such an embodiment, arm 181 may be required to wait for arm 182 to complete high priority tasks before arm 181 progresses to its next step or location in space. More complicated dynamic prioritization strategies may be employed in sophisticated liquid handling techniques. In the exemplary embodiment employing a strategy in which arm 182 has permanent priority, arms 181,182 may be synchronized to coordinate motions for maximal movement efficiency. It will be appreciated that the particular synchronization strategy employed may be application specific, and accordingly may be affected by the number of samples, compounds, or other reagents to be drawn and dispensed, the number of stations 121-124 in use on platform 129 for a particular application, the number and length of mixing operations to be conducted, the rapidity with which discrete sample mixtures are injected into the analysis apparatus, and other factors.

Arm 181 may address compound plate stations 122 used for agonist mode, antagonist mode, allosteric modulator mode, or various other operational or experimental modalities and protocols. Compounds or reagents may be taken up into pipette tip 188 and added to cell samples or buffer (for dilution purposes) in a predetermined or selected well of a microwell plate at a selected station 122. Mixing of cell sample material and compound or compound and buffer may be performed by arm 181 and probe 183, for example, through selective use of syringe 153 alternatively to draw a mixture from a microwell and to expel the mixture. In some embodiments, a single such cycle may be sufficient to provide adequate mixing, though a mixing cycle may be omitted in some instances, for example, or repeated for any desired number of iterations.

Specifically, arm 181 and probe 183 may address a suspension of viable cell samples and subsequently draw a selected or predetermined sample volume of evenly suspended cells into pipette tip 188 for delivery to a selected well of the microwell plate, i.e., arm 181 and probe 183 may be used to dispense the cell sample volume into microwell plate. Further, arm 181 and probe 183 may be implemented to mix the contents of a specific well (for example, by pipetting up and down a selected or predetermined number of times) without substantially disturbing the cells in the context of the parameters to be measured (e.g., intracellular $Ca^{2+}$). Alternatively, the injection of cell samples into the well may be sufficient for mixing, eliminating the need for additional pipetting. The cell suspension mixture may then be left in the mixing well until the contents are withdrawn by arm 182 and probe 184 for injection to an analysis apparatus.

After mixing the cell samples and compound for a particular well (i.e., preparing a discrete sample mixture), arm 181 may then travel to waste bag station 124 and automatically eject pipette tip 188 from probe 183. In some embodiments, tip ejection may be monitored, for example, by an IR or other suitable sensor or camera to ensure proper and complete ejection of pipette tip 188. In the case of incomplete ejection, buffer may be rapidly flushed through probe 183 and pipette tip 188, and ejection procedures may be repeated until pipette tip 188 is removed from probe 183. Following confirmation of proper tip ejection, arm 181 may be manipulated to return probe 183 to tip rack 121 (or to a different tip rack) to retrieve a new pipette tip 188 in preparation for the next task.

As noted above, arm 182 and probe 184 may withdraw the cell material and compound (a discrete sample mixture) into a pipette tip 188 after an appropriate, predetermined, or otherwise selected duration following mixing; arm 182 and probe 184 may then engage pipette tip 188 with sample injection guide 139 (as illustrated in FIG. 5) and transfer the discrete sample mixture to flow cytometer 190 (or to another sample analysis apparatus).

Regarding injection of discrete sample mixtures into an independent fluidic system, it is noted that FIGS. 9, 10, 11, and 12 are simplified diagrams illustrating perspective, plan, side elevation, and axial cross-section views, respectively, of one embodiment of a sample injection guide. Additionally, as noted above, FIG. 5 is a simplified diagram illustrating a perspective view of one embodiment of a sample injection guide engaged with a pipette tip during use.

Guide 139 and its various components may be fabricated of virtually any suitably non-reactive material. In this context, "non-reactive" generally refers to materials which will not adversely affect the experimentation occurring in the analysis apparatus. In one embodiment, for example, guide 139 may be fabricated of DELRIN™ plastic, though other plastics, acrylics, fiberglass, metals, and other materials may also be suitable.

As indicated in the drawing figures, one embodiment of guide 139 may generally comprise a guide well 135 dimensioned and operative to receive or otherwise sealingly to engage pipette tip 188, and a port 136 in fluid communication with both guide well 135 and the fluidic system of the analysis apparatus. During injection operations, pipette tip 188 may be engaged or seated in guide well 135 such that liquid or air cannot leak through the area of contact between guide well 135 and pipette tip 188. In that regard, it will be appreciated that the general constitution and specific dimensions of guide well 135 (e.g., depth, internal diameter, and taper) may be selected in accordance with the type of pipette tip 188 with which it is intended to be used. For example, guide well 135 is illustrated as tapered in FIGS. 11 and 12; in some embodiments, taper or angular dimensions provided for guide well 135 may be specifically designed to cooperate with a corresponding and complementary tapered portion of pipette tip 188.

When pipette tip 188 is engaged with guide well 135 as set forth above, a discrete sample mixture, or other contents of pipette tip 188, may be injected through port 136 into the fluidic system of the analysis apparatus. Port 136 may be coupled to an independent fluidic system, for example, using flexible tubing, hose barbs, quick-disconnect assemblies, and other types of fluid coupling hardware and mechanisms generally known in the art. This "connection" between port 136 and the independent fluidic system has been omitted from the drawing figures for clarity.

When pipette tip 188 is withdrawn from guide well 135, the free stream dynamic pressure of the independent fluidic system may force liquid back through port 136 and into guide well 135, flushing the connection, port 136, and guide well 135. This flushing may prevent residual material from one discrete sample mixture from contaminating a subsequent discrete sample mixture and altering or otherwise affecting the analysis thereof. It will be appreciated that the dynamic pressure associated with the fluidic system may cause flooding and overflow of guide well 135; additionally, removing liquid back flushed through port 136 into guide well 135 may facilitate minimization of deleterious contamination between successive sample mixtures. Accordingly, some embodiments of guide 139 may additionally comprise an overflow well 134 and siphon ports 137,138.

During operation, back pressure from the independent fluidic system generally causes fluid to flush through port 136 and into guide well 135 and overflow well 134. The depth of fluid in guide well 135 and overflow well 134, on the other hand, may exert sufficient hydrostatic pressure to balance the pressure of the fluid entering wells 135,134 through port 136, preventing a spray or "geyser" effect and minimizing liquid waste. Back flushed liquids (and any sample cells, reagents, or other contamination carried therein) may be siphoned, either by gravity alone, for example, or by pumping mechanisms, through siphon ports 137,138.

It will be appreciated that the structural characteristics, relative dimensions, locations, and orientations of the various elements (i.e., wells 134,135, ports 136-138, and siphon pumps, if implemented) may be selected in accordance with the type of independent fluidic system employed and the operational dynamic pressures expected. For example, an additional siphon port may be required in some instances; alternatively, one or both of siphon ports 137,138 may be omitted. Where no siphon ports are provided, guide well 135 or overflow well 134 may simply be allowed to overflow into a waste drain or bag, for example, or a siphon tube which is not integrated into the structure of guide 139 may be employed.

In the exemplary embodiment, for instance, excess liquid not siphoned from overflow well 134 by siphon ports 137,138 may be directed to a channel 131, where it may then be drained to an appropriate waste container or drain through ports 132,133. Additionally or alternatively, one or both of ports 132,133 may be employed, for example, as guide holes for screws, bolts, or other fastening members, to facilitate attachment of guide 139 to platform 129 or to the analysis apparatus. The present disclosure is not intended to be limited by the structural configuration and design characteristics of guide 139 illustrated in FIGS. 5 and 9-12. It will be appreciated that numerous alterations may be made to guide 139, and that the functionality described herein not limited to the design depicted in the drawing figures.

In accordance with the exemplary embodiment, guide 139 may satisfy the functional requirements set forth below. As best illustrated in FIG. 5, guide 139 may serve as a docking port between a pipette tip 188 containing a discrete sample mixture and an input port (not shown) of flow cytometer 190 or any other sample analysis apparatus employed in conjunction with system 100. In the case of flow cytometer 190, for instance, such an input port may be embodied in or comprise a tube in fluid communication with a flow nozzle or cuvette. Guide 139 may have particular utility in cases where hydrodynamic focusing between the discrete sample mixture (injected by pipette tip 188 through guide 139) and sheath fluid in the fluidic system of the analysis apparatus occurs at the input port of the analysis apparatus or just downstream thereof.

In particular, guide 139 may allow the contents of pipette tip 188 to be directly injected through port 136 into flow cytometer 190 (or to any independent fluidic system) on a discrete sample-by-sample basis. Operation of guide 139 enables contents of pipette tip 188 (i.e., a discrete sample mixture) to be treated as, and to behave as, the ideal sample stream described in conventional flow cytometry applications, i.e., where individual sample tubes are manually placed at the sample input station.

Additionally, guide 139 may permit rapid flushing of the sample input tubing (e.g., the input port of the analysis apparatus) to remove adherent compounds and residual sample material from the previous sample mixture. It will be appreciated that the tubing connecting guide 139 (at port 136) to the flow nozzle (i.e., associated with the fluidic system of the analysis apparatus) ideally needs to be washed free of contamination between successive discrete samples; such flushing may prevent sample carryover artifacts in the data stream. To achieve this flushing between successive discrete sample input operations, as set forth in detail above, port 136 and guide well 135 may be in continuous fluid communication with the normal sheath fluid used in the fluidic systems of standard flow cytometers. When pipette tip 188 is disengaged from guide well 135, the sheath fluid of the independent fluidic system (that is normally under positive pressure) washes backwards through port 136. This reverse flow serves to wash the connector tube and the port 136. As set forth above, excess fluid may be removed by gravity, for example, or by continuous aspiration (such as by a vacuum pump) through siphon ports 137,138 and channel 131.

As set forth in detail above, guide 139 may facilitate docking or engagement of pipette tip 188 and guide well 135, allowing pipette tip 188 to be firmly and tightly sealed with the walls of guide well 135; additionally, guide 139 may be operative to prevent the force of docking (i.e., the engagement of pipette tip 188 with guide well 135) from disturbing the alignment between the cells in the sample mixture stream and the lasers of flow cytometer 190 or other equipment in the analysis apparatus. In some embodiments, the foregoing alignment may be achieved by utilizing a length of flexible tubing that communicates sample mixtures from port 136 to the independent fluidic system. Such flexible tubing may absorb stresses associated with repeated engagement of pipette tip 188 with guide well 135, and may prevent transmission of those stresses to components of the analysis apparatus. Maintaining alignment in the foregoing manner may ensure continuous data consistency and quality throughout repeated runs of successive experiments.

Delivery of a discrete sample mixture to the analysis apparatus may be controlled by the pipetting syringe 154 operatively coupled to probe 184 on arm 182 and, in turn, by a motor (such as a servo motor or equivalent device) driving syringe 154. Injection of a discrete sample mixture through port 136 may selectively be rapid and of brief duration, for example, or alternatively, slow and prolonged. In the exemplary embodiment, sample mixture injection rates may be selectively controlled, for example, through control of the servo motor, and thereby the dispense rate of syringe 154. Similarly, pipetting functionality for arm 181 and probe 183, including volumes and rates, may be controlled by a servo-motor driving syringe 153. As set forth above, such control may be effectuated through appropriate programming instructions for processing component 170.

When an injection cycle is completed (i.e., a discrete sample mixture has been injected through guide 139 to an independent fluidic system) arm 182 and probe 184 may move to a waste bag station 124 and eject pipette tip 188 to a waste container substantially as described above with reference to arm 181 and probe 183. As with the foregoing ejection procedure, ejection of pipette tip 188 from probe 184 may be monitored (e.g., by a sensor or camera) to ensure successful ejection of pipette tip 188. Respective arms 181,182 and probes 183,184 may be prepared for the next cycle by retrieving new pipette tips 188 from designated or selected tip racks 121.

In accordance with FIG. 15 embodiment, cell sample material to be analyzed may be maintained in suspension by an active cell suspension system (CSS) 140. During operation, CSS 140 may prevent the cells from settling and, accordingly, may keep cell material at a constant density throughout the entire suspension volume. In that regard, CSS 140 may generally comprise a tube 141 mounted to a rocking apparatus 145. Tube 141 may be loaded with cells and a liquid suspension medium, and generally comprises an aperture 142 allowing access to the contents thereof by pipette tip 188. Tube 141 and its contents may be rocked by rocking apparatus 145 from an horizontal position alternately to positions approximately +/−45 degrees off the horizontal axis. In some instances, rocking may be controlled such that CSS 140 does not agitate the suspension in such a manner as to perturb resting cell physiology as measured by fluorescent probes that indicate, for example, $Ca^{2+i}$ membrane potential or plasma membrane integrity.

By way of example, a suspension vessel, such as tube 141, may be a 50 ml sealable plastic tube (e.g., as may be available from Falcon Labware or various other manufacturers), though specific dimensions, volume, and material may be varied as desired. As noted above, tube 141 generally comprises an access port or aperture 142 allowing pipette tip 188 coupled to probe 183 to access the cell suspension in tube 141. In some embodiments, CSS 140 in general, and rocking apparatus 145 in particular, may be under control of processing component 170; responsive to an appropriate control signal from processing component 170, for example, operation of rocking apparatus 145 may be interrupted, and tube 141 may be maintained in a desired orientation, while pipette tip 188 coupled to probe 183 approaches tube 141, enters aperture 142, and withdraws a selected volume of cell sample material. Responsive to an additional signal from processing component 170, or following a predetermined or selected duration, rocking action may be resumed following withdrawal of pipette tip 188 from aperture 142.

Figure 3:
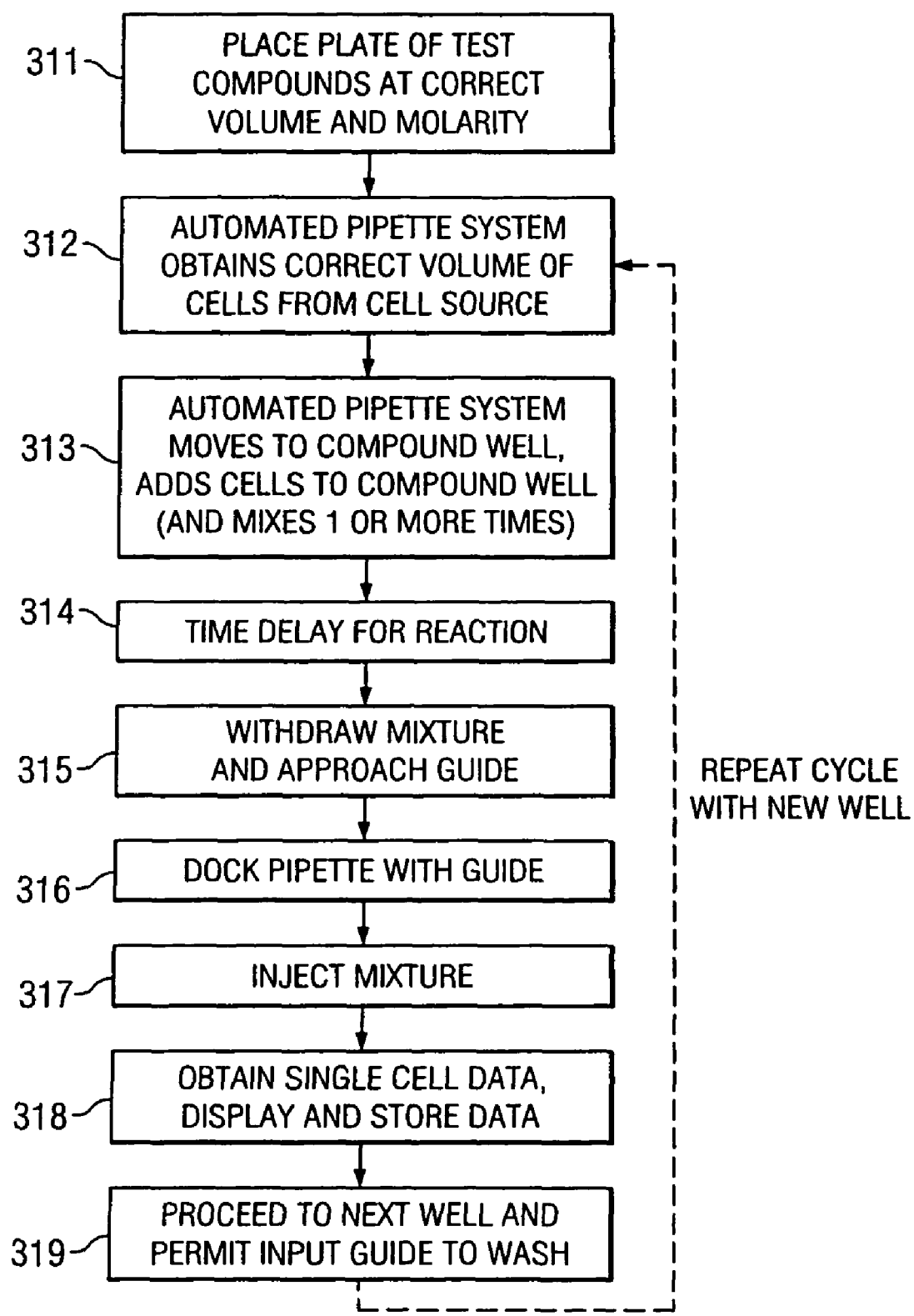
FIG. 3 is a simplified flow diagram illustrating the general operation of one embodiment of a method of performing an analysis using a direct sample injection system.

FIG. 3 is a simplified flow diagram illustrating the general operation of one embodiment of a method of performing an analysis using a direct sample injection system. At the initiation of any particular analysis method, as indicated at block 311, a plate of test compounds (at any desired or selected volume and molarity) may be placed at a selected or predetermined station 122 on platform 129; additionally or alternatively, a rack of test tubes, each of which may contain one or more compounds of a selected volume and molarity, may be placed at a selected or predetermined station 123 on platform 129. As set forth above, any number of microwell plates or test tube racks containing various compounds or reagents, or desired combinations thereof, may be placed at one or more such stations 122,123 on platform; specifically, the operation depicted at block 311 may be repeated as desired any number of times and in accordance with a particular analysis protocol. Locations (i.e., at stations 122 or 123 on platform 129) of specific microwell plates or test tubes, as well as the specific contents of each well or test tube and associated data and parameters, may be input or otherwise recorded, for example, using software or other instruction sets, in processing component 170 for further reference, to program sequences of operations executed by arms 181,182 and probes 183,184, and the like.

As indicated at block 312, an automated pipetting apparatus (such as liquid handler 180, for example) may obtain a predetermined or preselected volume of cell material and suspension medium (e.g., from CSS 140). In some embodiments, instructions governing or otherwise influencing the operation depicted at block 312 may be provided by processing component 170 or an equivalent controlling mechanism adapted to provide commands to automated or semi-automated electromechanical systems; additionally or alternatively, such instructions may be provided, in whole or in part, in accordance with user intervention. In the exemplary FIG. 14 implementation, such retrieval of sample cell material may be effectuated by a dedicated pipetting arm 181 and associated hardware, though various other pipetting arm implementations are also contemplated.

Notwithstanding which of a plurality of pipetting arms (such as arms 181,182, for instance) performs the operation at block 312 (or whether a single arm liquid handler 180 is employed), sample material may be added or provided to a specified or predetermined compound well (at station 122) or test tube (at station 123) as indicated at block 313. Specifically, the operation at block 313 represents preparation of a discrete sample mixture (i.e., a mixture comprising a desired volume of sample material obtained from a common sample source (such as from suspension vessel or tube 141, for example) and a specified or preselected compound, reagent, buffer solution, or some desired combination thereof) at a specified location (e.g., at station 122 or station 123) on platform 129. As further indicated at block 313, one or more mixing operations may be conducted. In some instances (depending, for example, upon analysis protocols, the specific chemistry of discrete sample mixtures, and other factors), the foregoing providing sample material to a well or test tube may also effectuate necessary or desired mixing. Alternatively, mixing may be performed through one or more pipetting cycles wherein the discrete sample mixture (of sample material and compound or other chemical components in selected well or test tube) is alternately withdrawn and subsequently returned to the appropriate well or test tube. Again, the operation depicted at block 313 may be influenced or controlled by processing component 170, either automatically or in accordance with user intervention, and driven by a pump system (such as represented by reference numeral 151 in FIG. 15).

As indicated at block 314, a time delay may be provided to allow sufficient time for desired reactions to take place for a particular discrete sample mixture. In some embodiments, such a delay time may be identical, or substantially so, for each discrete sample mixture prepared as set forth above. Alternatively, reaction time durations for one or more discrete sample mixtures may vary from other discrete sample mixtures prepared on platform 129 and awaiting injection into the analysis apparatus. It will be appreciated that synchronization considerations, prioritization strategies, or both, for pipetting arm motions may be influenced or otherwise affected in accordance with the various reaction times required by, or desired for, each discrete sample mixture to be prepared and provided to the analysis apparatus. Accordingly, delay times may be recorded and monitored by processing component 170, for example, and liquid handler 180 may be controlled appropriately to accommodate various reactions and delay durations.

Following a desired or predetermined delay period (block 313) a discrete sample mixture may be withdrawn from its well or test tube station (122 or 123) for delivery or approach to sample injection guide 139 as indicated at block 315. Specifically, each discrete sample mixture prepared in a particular location on platform 129 may be individually addressed and withdrawn successively by liquid handler 180 in accordance with instructions provided, for example, by processing component 170. As illustrated in the drawing figures and described in detail above, an exemplary direct injection system may employ a clean pipette tip 188 for the operation depicted at block 315, eliminating or minimizing contamination between successive injection operations (blocks 316 and 317).

As indicated at blocks 316 and 317, a discrete sample mixture may be injected into the fluidic system of an analysis apparatus substantially as set forth above with specific reference to FIGS. 5 and 9-12. In particular, a pipette tip 188 containing a discrete sample mixture may be docked or sealingly engaged with a sample injection guide 139 (block 316); the discrete sample mixture may then be provided through guide 139 to an independent fluidic system (block 317) associated with a sample analysis apparatus (such as flow cytometer 190). As noted above, an injection rate for a particular discrete sample mixture may be selectively controlled, for example, through operation of a pump system (such as indicated at reference numeral 152) under control of processing component 170.

Data regarding a discrete sample mixture may be recorded, for example, on computer readable media at processing component 170, at another electronic device, or both, for storage or analysis; additionally, such data may be transmitted, via recording media or network data transmissions, for instance, to any desired computerized device or data processing apparatus for recordation or for further analysis. Appropriate, desired, or relevant data relating to the foregoing operations described with reference to blocks 311-315 and 317 may include, but not be limited to, some or all of the following information associated with a particular discrete sample mixture: specific chemistries, volumes, percentages, concentrations, compositions, or other factors related to the discrete mixture of cell samples, compounds, reagents, and buffer solutions; mixing parameters such as the number of pipetting cycles performed, for example, and the forcefulness or rapidity (in terms of fluid flow rates, for example) with which those cycles were executed; the time delay allowed between preparation of the discrete sample mixture and injection of same to the analysis apparatus; the time at which the particular discrete sample mixture is injected into the analysis apparatus, as well as the rate (or duration) of the injection process; and any other parameter monitored or controlled by processing component 170. It will be appreciated that the nature and relevance of data recorded in conjunction with the foregoing processes may be a function of the particular experiment or assay occurring in the analysis apparatus.

Further data may be obtained in accordance with standard or modified operation of the analysis apparatus as indicated at block 318. Though the present disclosure is not intended to be limited to any particular analysis apparatus, or to the operational characteristics or limitations thereof, it is noted that the operation depicted at block 318 may be executed by a flow cytometer 190, for example, or by any other sample analysis equipment known in the art or developed and operative in accordance with known principles of fluidic systems. Data acquired by the analysis apparatus (block 318) may be combined or otherwise associated with the data recorded as set forth above (in conjunction with blocks 311-315 and 317) at processing component 170 or elsewhere; alternatively, separate data files may be maintained for storage or processing as desired.

As indicated at block 319 and the dashed line returning to block 312, the foregoing operations may be executed any number of times, and for any number of discrete sample mixtures sought to be analyzed. As set forth above, processing component 170, or equivalent mechanisms, may be used to record the locations of discrete sample mixtures prepared, and those which have been analyzed versus those that have not.

As set forth above, guide 139 and any attendant coupling tubing or other fluid conduit connecting same to the independent fluidic system may be washed, for example, through a back flush of sheath fluid through operative portions of guide 139. This wash operation, set forth above with specific reference to FIGS. 5 and 9-12, is also depicted at block 319.

Figure 4:
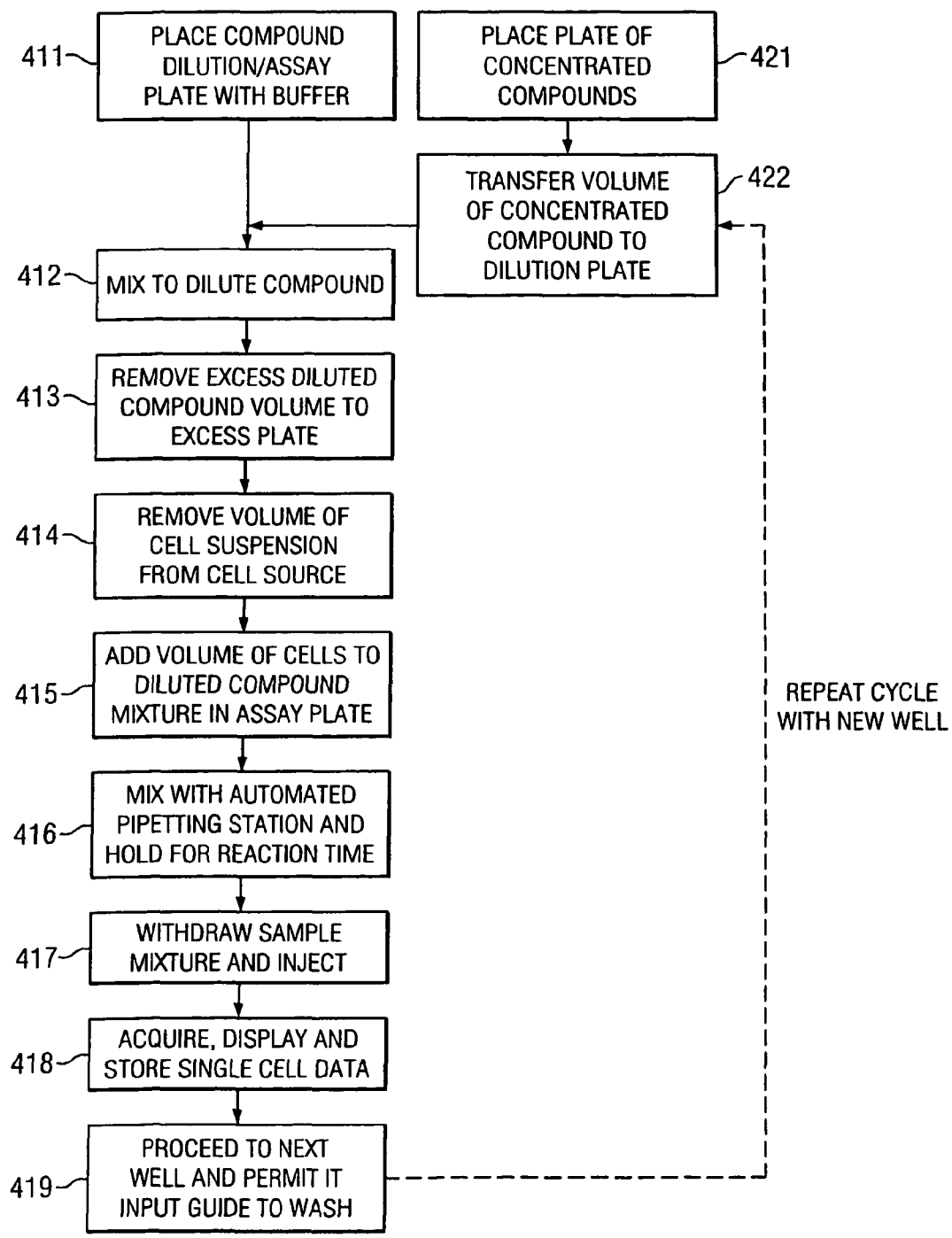
FIG. 4 is a simplified flow diagram illustrating the general operation of another embodiment of a method of performing an analysis using a direct sample injection system.

FIG. 4 is a simplified flow diagram illustrating the general operation of another embodiment of a method of performing an analysis using a direct sample injection system. At the initiation of any particular analysis method, as indicated at blocks 411 and 421, various plates or racks of test tubes containing compounds and buffer solutions (at any desired or selected volume and molarity) may be placed at selected or predetermined stations 122,123 on platform 129. As with the method described above, any number of microwell plates or test tubes containing various compounds, reagents, buffers, or desired combinations thereof, may be placed at one or more such stations 122,123 on platform. Appropriate data representative of locations of specific microwell plates or test tubes, as well as the specific contents thereof, may be input or otherwise recorded at processing component 170 or elsewhere. These data may be employed for further reference, to program sequences of operations executed by arms 181,182 and probes 183,184, and the like.

As indicated at blocks 412 and 422, an automated pipetting apparatus (such as liquid handler 180, for example) may transfer one or more compounds to selected other wells or test tubes at specified locations on platform; the resulting combination of liquids may be mixed as indication at block 412. In some embodiments, instructions governing or otherwise influencing the operations depicted at blocks 412 and 422 may be provided by processing component 170 or an equivalent controlling mechanism; additionally or alternatively, such instructions may be provided, in whole or in part, in accordance with user intervention. Mixing at block 412 may proceed substantially as set forth above with specific reference to block 313 in FIG. 3.

Following mixing of desired components, excess liquid may be removed from a specific well or test tube (block 413) to ensure that the particular well contains an appropriate amount of compound, reagent, buffer, and the like, for creating the desired discrete sample mixture for that particular well or test tube. Excess liquid withdrawn as contemplated at block 413 may be discarded as waste. The operation depicted at block 413 may be selectively controlled in accordance with desired sample analysis protocols for a particular experiment, in whole or in part, by processing component 170.

The operations depicted at blocks 414-416 (i.e., removing or obtaining a desired volume of cell sample material from a source such as CSS 140, for example, adding same to a desired well or test tube, mixing, and allocating a desired delay time), may proceed substantially as set forth above with specific reference to blocks 312-314 in FIG. 3. Specifically, the operations at blocks 414-416 represent preparation of a discrete sample mixture comprising a desired volume of sample material obtained from a common sample source (such as from suspension vessel or tube 141, for example) and a specified or preselected compound, reagent, buffer solution, or some desired combination thereof. This discrete sample mixture may be prepared and maintained at a specified location (e.g., at station 122 or station 123) on platform 129.

As further indicated at block 416, one or more mixing operations may be conducted. Such operations may depend, for example, upon analysis protocols, the specific chemistry of discrete sample mixtures, and other factors substantially as described above. Mixing may not be required in some applications. Further, a time delay may be provided to allow sufficient time for desired reactions to take place for a particular discrete sample mixture. While such a delay time may be identical, or substantially so, for each discrete sample mixture, reaction time delays for one or more discrete sample mixtures may vary from other discrete sample mixtures. Accordingly, synchronization considerations, prioritization strategies, or both, for pipetting arm motions may be influenced or otherwise affected. Where required, one or both of the operations depicted at block 416 may be influenced or controlled by processing component 170, either automatically or in accordance with user intervention.

The operations depicted at blocks 417-419 (i.e., withdrawing and injecting a discrete sample mixture, acquiring data from an analysis apparatus, and reiterating the procedure), may proceed substantially as set forth above with specific reference to blocks 315-319 in FIG. 3. In particular, a discrete sample mixture may be retrieved by liquid handler 180 and injected (block 417) into the fluidic system of an analysis apparatus as described above with specific reference to FIGS. 5 and 9-12. In that regard, a pipette tip 188 containing a discrete sample mixture may be docked or sealingly engaged with a sample injection guide 139; the discrete sample mixture may then be provided through guide 139 to an independent fluidic system associated with a sample analysis apparatus (such as flow cytometer 190). An injection rate or duration for a particular discrete sample mixture may be selectively controlled, for example, through operation of a pump system (such as indicated at reference numeral 152) under control of processing component 170.

Relevant or desired data associated with a discrete sample mixture may be recorded, transmitted, or both, for example, under control of processing component 170 substantially as set forth above. As in the FIG. 3 embodiment, these data may include: specific chemistries, volumes, percentages, concentrations, compositions, or other factors related to the discrete mixture of cell samples, compounds, reagents, and buffer solutions; mixing parameters; the time delay; the time (and rate) at which the particular discrete sample mixture is injected into the analysis apparatus; and any other parameter monitored or controlled by processing component 170. The nature and relevance of data acquired, recorded, or otherwise manipulated in conjunction with the foregoing processes may be a function of the particular experiment or assay occurring in the analysis apparatus.

Additional data may be acquired in accordance with standard or modified operation of the analysis apparatus as indicated at block 418. Finally, as indicated at block 419 and the dashed line returning to block 422, the foregoing operations may be iterated any number of times, and for any number of discrete sample mixtures sought to be analyzed. Processing component 170, or equivalent mechanisms, may be used to record the locations of discrete sample mixtures prepared, and those which have been analyzed versus those that have not. Guide 139 and any attendant coupling or fluid conduit connecting same to the independent fluidic system may be washed, for example, through a back flush of sheath fluid through operative portions of guide 139. This wash operation, set forth above with specific reference to FIGS. 5 and 9-12, is also depicted at block 419.

The specific arrangement and organization of functional blocks depicted in FIGS. 3 and 4 are not intended to be construed as implying any particular order or sequence of operations to the exclusion of other possibilities. Alternative sequences, combinations and simultaneous execution of various operations are also contemplated, and may be enabled or facilitated, for example, in multiple arm liquid handler embodiments and during successive iterations of sample injection cycles. For example, the operations depicted at blocks 315-319 with respect to one sample mixture may occur in parallel, or substantially simultaneously, with operations 312-314 conducted with respect to a different or subsequent iteration for a next successive or different discrete sample mixture. Similarly, the operations depicted at blocks 422 and 412-416 (with respect to one sample mixture) may be executed in parallel, or substantially simultaneously, with the operations depicted at blocks 417-419 (with respect to a sample mixture previously prepared). Those of skill in the art will appreciate that the operations depicted at blocks 317 and 318 may occur substantially simultaneously; similarly, the injection operation (block 417) and the acquisition operation (block 418) depicted in FIG. 4 may also be executed substantially simultaneously.

Figure 16:
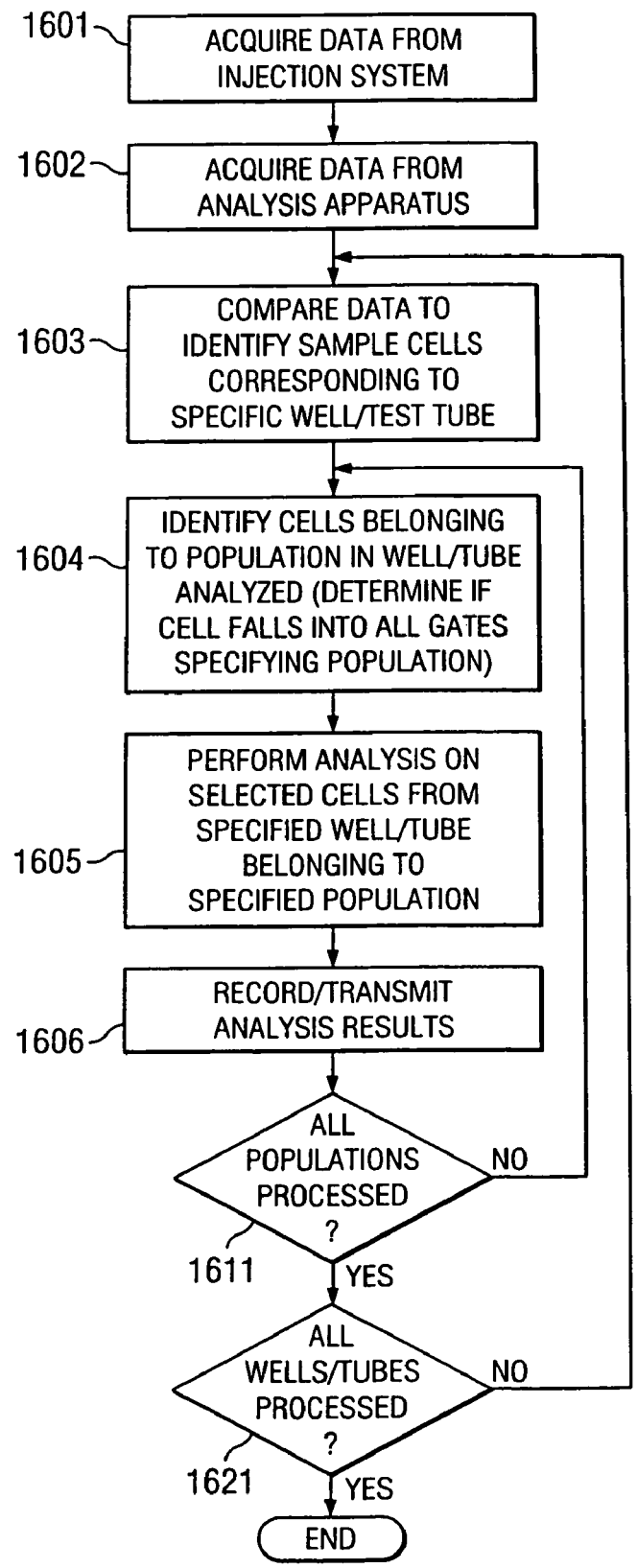
FIG. 16 is a simplified flow diagram illustrating the general operation of one embodiment of a method of performing an analysis.

FIG. 16 is a simplified flow diagram illustrating the general operation of one embodiment of a method of performing an analysis. As indicated at blocks 1601 and 1602, data may be acquired from a sample injection system (such as by processing component 170, for example) and from an analysis apparatus substantially as set forth above with specific reference to FIGS. 3 and 4. Acquired data may then be compared (block 1603) to identify which data records obtained by the sample analysis apparatus correspond with data records obtained and recorded by the injection system associated with a particular discrete sample mixture. Where an injection time and rate for a particular sample mixture are recorded by processing component 170, for example, data acquired by the analysis apparatus at that time and for a specific duration thereafter may be flagged as associated with that particular discrete sample mixture. In the foregoing manner, data from the analysis apparatus may be correlated with data from the injection system such that data records may be matched and associated with a specific discrete sample mixture. This correlation may be have particular utility in ascertaining which analysis results are obtained from the sample mixture in a particular well or test tube; in some applications, correlating analysis results with the composition of a sample mixture may facilitate interpretation of the results.

As indicated at block 1604, cell sample material belonging to a particular population may be identified and associated with a specific well or test tube from which the sample mixture was prepared and drawn. In accordance with one embodiment, for example, the identification of cells within a population may comprise determining if a cell falls into all gates specifying the population sought to be identified. It will be appreciated that these gates, and other sorting criteria or parameters, may be user-specified and application specific. In the foregoing manner, cells within a particular well or test tube may be associated with the population criteria appropriate or desired for a particular experiment.

A selected or desired analysis may then be performed on selected cells from a particular well or test tube (i.e., discrete sample mixture) that are identified as belonging to or associated with a particular population as indicated at block 1605. Various analyses including statistical analytical techniques are contemplated at block 1605. For example, mean intensity, median intensity, percentage of cells exceeding a predetermined threshold intensity value, and the like, may be appropriate or desired. It will be appreciated that the nature of the analysis performed at block 1605, as well as the nature of the data records acquired in conjunction with its execution, may vary in accordance with some or all of the following, without limitation: the type of analysis apparatus employed; the functional characteristics and limitations thereof; the operational modality or parameters set to control the analysis apparatus; the type of experiment conducted; and other factors.

Data acquired during the analysis at block 1605 may be recorded, transmitted, processed, or otherwise manipulated as generally indicated at block 1606. Recorded data records may be saved or stored, for example, on computer readable media for processing at a later time; additionally or alternatively, data processing may occur simultaneously or in conjunction with the recordation depicted at block 1606. As set forth above with reference to FIGS. 3 and 4, data may be transmitted via recording media, for instances, or via network data communications to any desired computerized device or processing apparatus.

As indicated by the decision blocks 1611 and 1621, the foregoing process may be selectively iterated, for example, until all populations and all discrete sample mixtures have been analyzed. The iterative nature of the FIG. 16 embodiment may be selectively interrupted in accordance with user intervention if desired.

Aspects of the present invention have been illustrated and described in detail with reference to particular embodiments by way of example only, and not by way of limitation. It will be appreciated that various modifications and alterations may be made to the exemplary embodiments without departing from the scope and contemplation of the present disclosure. It is intended, therefore, that the invention be considered as limited only by the scope of the appended claims.

What is claimed is:

1. A sample analysis system comprising:
 a liquid handling apparatus operative to prepare a discrete sample mixture, wherein the liquid handling apparatus comprises a coupling component that is operative to accommodate disposable pipette tips, and wherein the coupling component enables automatic ejection of the disposable pipette tips;
 wherein the coupling component comprises an exterior portion operative to engage, under pressure, a cooperating open end of a disposable pipette tip, and an interior portion that includes a conical recess at a distal end of the coupling component;
 a sample analysis apparatus; and
 an injection guide coupled to said analysis apparatus; said injection guide operative to receive said discrete sample mixture from said liquid handling apparatus and to provide said discrete sample mixture to a fluidic system of said analysis apparatus.

2. The system of claim 1 wherein said injection guide comprises:
 a guide well operative to engage a pipette tip manipulated by said liquid handling apparatus; and
 a port in fluid communication with said guide well and operative to receive said discrete sample mixture from said pipette tip and to communicate said discrete sample mixture to said fluidic system.

3. The system of claim 2 wherein said guide well and said port are in continuous fluid communication with said fluidic system.

4. The system of claim 1 wherein said liquid handling apparatus comprises a single arm liquid handler.

5. The system of claim 1 wherein said liquid handling apparatus comprises a multiple arm liquid handler.

6. The system of claim 1 wherein said multiple arm liquid handler employs two pipetting arms.

7. The system of claim 1 further comprising a cell suspension system operative to maintain sample cell material at a substantially constant density throughout a volume of suspension medium.

8. The system of claim 7 wherein said cell suspension system comprises:
 a suspension vessel containing said sample cell material and said suspension medium; and
 a rocking apparatus operative to agitate said sample cell material and said suspension volume in said suspension vessel.

9. The system of claim 8 wherein said suspension vessel comprises a sealed tube having an aperture; said aperture allowing a component of said liquid handling apparatus to withdraw a volume of said sample cell material and said suspension volume from said tube.

10. A sample analysis system comprising:
 a liquid handling apparatus operative to prepare a discrete sample mixture, wherein the liquid handling apparatus comprises a coupling component that is operative to accommodate disposable pipette tips, and wherein the coupling component enables automatic ejection of one or more disposable pipette tips;
 wherein the coupling component comprises an exterior portion operative to engage, under pressure, a cooperating open end of a disposable pipette tip, and an interior portion that includes a conical recess at a distal end of the coupling component;
 a sample analysis apparatus, wherein said sample analysis apparatus comprises a flow cytometer; and
 an injection guide coupled to said analysis apparatus; said injection guide operative to receive said discrete sample mixture from said liquid handling apparatus and to provide said discrete sample mixture to a fluidic system of said analysis apparatus.

11. A sample analysis system comprising:
 a liquid handling apparatus operative to prepare a discrete sample mixture, wherein the liquid handling apparatus comprises a coupling component; said coupling component being operative to accommodate disposable pipette tips wherein the coupling component comprises an exterior portion operative to engage, under pressure, a cooperating open end of a disposable pipette tip, and an interior portion that includes a conical recess at a distal end of the coupling component;
 a mechanical ejector within the coupling component for automatically ejecting the disposable pipette tips;
 a sample analysis apparatus;
 an injection guide coupled to said analysis apparatus; said injection guide operative to receive said discrete sample mixture from said liquid handling apparatus and to provide said discrete sample mixture to a fluidic system of said analysis apparatus; and a processing component operative to acquire a first data set associated with said discrete sample mixture from said liquid handling apparatus, to acquire a second data set associated with said discrete sample mixture from said sample analysis apparatus, to compare said first data set with said second data set to correlate data records with said discrete sample mixture, and to perform an analysis on said data records associated with said discrete sample mixture.

12. The system of claim 11 wherein said injection guide comprises:
   a guide well operative to engage a pipette tip manipulated by said liquid handling apparatus; and
   a port in fluid communication with said guide well and operative to receive said discrete sample mixture from said pipette tip and to communicate said discrete sample mixture to said fluidic system.

13. The system of claim 12 wherein said guide well and said port are in continuous fluid communication with said fluidic system.

14. The system of claim 11 wherein said processing component is further operative to control said liquid handling apparatus.

15. The system of claim 14 wherein said liquid handling apparatus comprises a single arm liquid handler.

16. The system of claim 14 wherein said liquid handling apparatus comprises a multiple arm liquid handler.

17. The system of claim 16 wherein said multiple arm liquid handler employs two pipetting arms cooperating under control of said processing component to prepare said discrete sample mixture.

18. The system of claim 11 further comprising a cell suspension system operative to maintain sample cell material at a substantially constant density throughout a volume of suspension medium.

19. The system of claim 18 wherein said processing component is further operative to control operation of said cell suspension system.

20. The system of claim 1, further comprising one or more disposable pipette tips.

21. The system of claim 20, wherein the coupling component and the disposable pipette tip, when sealingly engaged to form a juncture, prevent leakage at the juncture.

22. The system of claim 11, further comprising one or more disposable pipette tips.

23. The system of claim 22, wherein the coupling component and the disposable pipette tip, when sealingly engaged to form a juncture, prevent leakage at the juncture.

24. The system of claim 1, further comprising a mechanical ejector within the coupling component for automatically ejecting the disposable pipette tips.

* * * * *